(12) United States Patent
Esser et al.

(10) Patent No.: US 8,868,369 B2
(45) Date of Patent: Oct. 21, 2014

(54) GAIT MONITOR

(75) Inventors: Patrick Esser, Simpelveld (NL); Ken Howells, Headington (GB); Helen Dawes, Headington (GB); Johnny Collet, Headington (GB)

(73) Assignee: Oxford Brookes University, Oxford, Oxfordshire (GB)

( * ) Notice: Subject to any disclaimer, the term of this patent is extended or adjusted under 35 U.S.C. 154(b) by 613 days.

(21) Appl. No.: 13/141,834

(22) PCT Filed: Dec. 23, 2009

(86) PCT No.: PCT/GB2009/051767
§ 371 (c)(1),
(2), (4) Date: Sep. 12, 2011

(87) PCT Pub. No.: WO2010/073044
PCT Pub. Date: Jul. 1, 2010

(65) Prior Publication Data
US 2011/0313705 A1 Dec. 22, 2011

(30) Foreign Application Priority Data

Dec. 23, 2008 (GB) .................................. 0823374.4

(51) Int. Cl.
*A61B 5/11* (2006.01)
(52) U.S. Cl.
CPC ......... *A61B 5/112* (2013.01); *A61B 2562/0219* (2013.01); *A61B 5/1122* (2013.01)
USPC ....................................................... 702/104
(58) Field of Classification Search
CPC ....................................................... A61B 5/112
USPC ........................................................... 702/104
See application file for complete search history.

(56) References Cited

U.S. PATENT DOCUMENTS

| 6,162,191 A | 12/2000 | Foxlin |
| 6,853,947 B1 | 2/2005 | Horton |
| 2007/0032748 A1 | 2/2007 | McNeil et al. |
| 2008/0285805 A1 | 11/2008 | Luinge et al. |
| 2009/0079559 A1* | 3/2009 | Dishongh et al. ........ 340/539.13 |
| 2011/0218463 A1* | 9/2011 | Hodgins et al. ............... 600/595 |

FOREIGN PATENT DOCUMENTS

| DE | 10312154 A1 | 6/2004 |
| KR | 20050097181 A | 10/2005 |
| KR | 100620118 B1 | 9/2006 |

* cited by examiner

*Primary Examiner* — Bryan Bui
(74) *Attorney, Agent, or Firm* — Fraser Clemens Martin & Miller LLC; William J. Clemens

(57) ABSTRACT

Vertical center of mass movement measuring apparatus comprising an inertial sensing device, for producing outputs relating to rotation and acceleration in its local frame of reference and configured for fastening to the back of an animal, preferably a person, a memory and a processor, wherein the processor is programmed to provide a quaternion corresponding to the rotation of the inertial sensing device and a first acceleration, both based on an output of the rotation sensing device, and the processor is programmed to combine the quaternion and the first acceleration and based on the result of the combination to provide, when the device is fastened close enough to the center of mass of a moving object such as a person, an estimate of vertical displacement, or a derivative of vertical displacement, of the center of mass in a global reference frame.

23 Claims, 5 Drawing Sheets

GAIT MONITOR

BACKGROUND OF THE INVENTION (1) Field of the Invention (2) Description of Related Art This invention relates to an apparatus and method for measuring vertical movement by using inertial sensors, and in particular to an apparatus and method for inertial sensing of human centre of mass movement in the vertical direction.

The centre of mass (CoM) is an important aspect of human locomotion and it has long been estimated that measurements of the vertical displacement of the centre of mass of a human, represents over 65% of the total mechanical work done in gait, i.e., whilst walking.

Reasonably accurate estimations of a location of a centre of mass of a human body have existed since the $19^{th}$ Century from dissection of cadavers. This location has been measured more accurately in the $20^{th}$ Century, for example using force plates, and is generally found to be around the lower back.

Measurements of the displacement of a person's centre of mass are found to provide very useful information for studying a person's movement. This can be useful in clinical care, for example in the study of the elderly or disabled, and in particular in determining the effects of conditions which affect walking. Measurements of centre of mass movement in gait before and after surgery can be used to measure the surgery's success and to direct suitable physiotherapy.

Measurement of the movement of the centre of mass of a human is also considered to be very useful in study of athletes and can be used in coaching and for developing improved technique of the movement of athletes.

Measurement of the displacement of the centre of mass can show asymmetry in the manner in which someone walks. In addition even where the significance of the data in isolation is not well understood, simply comparing the patterns of centre mass displacement found in people of an ordinary gait with those of untypical walking patterns or in an effective Olympic athlete, provides useful feedback and allows alterations to be made.

Desired uses for a gait assessment tool are to assist in the diagnosis of a gait abnormality, to monitor patient progress, to take a baseline assessment and to assist with orthotic prescription.

The best present systems for biomechanical studies and for measuring kinematic data from humans are considered to be optical motion camera systems (OMCS). OMCS determine the position of an object in a three dimensional calibrated space. These systems include passive and active marker systems. For example the Vicon system produced in Oxford, UK has infra red reflecting markers attached to an object to contain kinematic data from cameras, whilst the CODA system used by Codamotion in the UK uses active LED sensors applied to the object to obtain similar data. These systems provide very effective and accurate data but suffer from a number of disadvantages. Firstly, and perhaps most significantly, they are very expensive. Secondly the measurements are restricted to movement within calibrated areas. This typically means that only a few strides can be measured at one time, thereby not permitting study of all types of human locomotion. Additionally it is advantageous to measure movement in outdoor experiments in an attempt to replicate movement in the real world. Outdoor measurements are difficult with OMCS systems due to the need for calibrated areas and are particularly difficult for many of the common systems that use infra red reflective light that struggle with too much ambient sunlight.

A cheaper alternative to using OMCS systems is to use force plates to measure the ground reaction forces and to attempt to calculate the centre of mass displacement form the ground reaction forces. Whilst this is of some use, it is found that ground reaction forces are not the same as the centre of mass displacement. In addition force plates are still expensive for the amount of measurement that can be obtained. Accurate force plates are also immobile and need to be placed on a solid flat surface. They are small and require a subject to ensure that they place their foot onto the forceplate and so may affect walking style. For accuracy they also require floors, walls and connections to be specifically made to have a vibrationless signal.

Accelerometers have also been used in movement analysis, particularly in pedometers which measure the number of strides a person takes. One difficulty with using accelerometers to measure human locomotion is that the circular paths created by human locomotion mean that the angle of the axis of the accelerometer is constantly changing. The twisting of the axis makes it very difficult to calculate accelerations in the global reference frame, i.e., in terms of up and down against the force of gravity. Postural alignment of the walking subject and inaccuracy in positioning of the instrument must be corrected for the static gravity in order to assess true dynamic acceleration in gait.

There also exists units, such as inertial measurement units, that combine accelerometers with gyroscopes and possibly also with magnetometers. These measure changes in orientation as well as accelerations in the local axes of the accelerometers. These therefore provide the vectors of acceleration of the local object system which potentially could be transposed into axis of another system. For these reasons a combination of accelerators, gyroscopes and in some cases industrial micro electro-mechanical (MEM) IMUs (typically used for vibration sensing) have been used to measure the change of angle in joints and in other aspects of human movement. There has also been an attempt to estimate the centre of mass displacement of horses using an IMU. This was reasonably successful given that millimeter accuracy is not required for typical study of horses and it has now been realised because the IMU located on the back of a horse stays reasonably horizontal the majority of the time reducing the likelihood of error in the Z axis resulting from mathematical gimbal lock.

It has been commonly assumed that using known accelerometers, gyroscopes and inertial measurement units on the back of a human to measure displacement in the global frame will not be possible for providing any useful degree of accuracy. This is based on the fact that whilst the IMUs do give accurate data for the accelerations and orientation movement regarding their local frame, there will be a very significant drop in accuracy in attempting to translate this information into movements in the global frame and a further loss of accuracy in moving from the measured acceleration to measures of speed and position which are the more common parameters required by clinicians and sports coaches. The axes of any unit near the Centre of Mass will turn and twist greatly making translation to a global reference frame difficult.

It is now realised by the inventors of the current invention that much of the inaccuracy in measuring vertical centre of mass displacement from an IMU comes from the fact that the IMU is placed on the lumbar spine so much of the data comes from the IMU being rotated through 90 degrees from its intended orientation and that use of an Euler angle rotation matrix leads to much of this data being lost due to mathematical gimbal lock. Further it has been surprisingly found that through correct use of suitable techniques it is possible to not only provide accurate measurement of vertical acceleration in the global reference frame but also speed and changes in position in the vertical direction. The accuracy can be almost comparable to that of optical motion camera systems.

Surveys of physiotherapists, find that in clinical practise only a small minority of respondents had actually had a patient assessed in a gait laboratory. Reasons for not using a gait assessment tool include lack of time, budget constraints and lack of space-all of which are due to the requirement of OMCS. Instead the physiotherapist mainly relies on Visual Gait Assessment Scales (VGAS) which are subjective and sometimes unreliable as they are reliant on an individual assessor's opinion of the abnormality and its severity.

It is also desirable to calculate how much energy a person (or animal) has used whilst walking or running. This information is useful for clinical purposes and also for anyone exercising who wished to calculate the number of calories used. Typically this is estimated by use of a pedometer and knowledge of the person's weight. The calculation are then simply based on weight and number of strides and take no account of the efficiency of gait, or of walking speed, or terrain. It has been realised that because such a large part of the energy used during walking is from moving the centre of mass vertically (against gravity), that measurements of the movement of centre of mass can be used alongside activity measures, such as step counts, to more accurately determine the amount of energy used running or walking. Conventional measurement equipment such as OMCS are of limited use for this. They can only measure in the calibrated space and therefore could only obtain useful information about energy consumed for a person over a very limited range or on a treadmill—where the speed of travel and inclination are already known and there is less pressing need for more accurate energy calculations. Further force and energy used can be based partly on accelerations or speed of the centre of mass and the OMCS provide data relating to position, which would have to be differentiated thereby reducing accuracy.

BRIEF SUMMARY OF THE INVENTION

It is an object of at least some embodiments of the invention to mitigate at least some of the above problems and/or to provide apparatus for measuring mechanical energy during human movement.

According to a first aspect of the invention there is provided a vertical movement measuring apparatus comprising an inertial sensing device, for producing outputs relating to rotation and acceleration in its local frame of reference, a memory and a processor, wherein the processor is programmed to provide a quaternion corresponding to the rotation of the inertial sensing device and a first acceleration, both based on an output of the rotation sensing device, and the processor is programmed to combine the quaternion and the first acceleration and based on the result of the combination to provide a measure of vertical displacement, or a derivative of vertical displacement, in a global reference frame.

According to a second aspect of the invention there is provided a vertical movement measuring apparatus comprising an inertial sensing device, for producing outputs relating to rotation and acceleration in its local frame of reference, a memory and a processor, wherein the processor is programmed to provide a rotation element such as an Euler rotation matrix and/or a quaternion, corresponding to the rotation of the inertial sensing device and a first acceleration, both based on an output of the rotation sensing device, and the processor is programmed to combine the rotation element and the first acceleration and based on the result of the combination to provide a measure of vertical displacement, or a derivative of vertical displacement, in a global reference frame.

Preferably the global reference frame is the reference frame of the earth's surface with the vertical direction being the direction of the acceleration of gravity.

Preferably the inertial sensing device is an inertial mass unit and/or contains multiple accelerometers (such as three) measuring linear accelerations in a local frame, and one or more gyroscopes (such as three) measuring rotational movement and preferably the device fuses their data outputs such as a by using Kalman filtering.

Preferably the apparatus is configured to filter the result(s) from the combination of the first acceleration and quaternion, such as the result of their product, above or below a predetermined frequency before producing a measure of vertical displacement, or a derivative of vertical displacement, in the global reference frame, more preferably the apparatus is configured to filter data out above a frequency chosen based on maximum walking or running stride frequency, such as 25 Hz and/or the apparatus comprises a Butterworth filter, such as in the form of suitable programming in the memory, which filter is configured to be used for the filtering.

Preferably the apparatus is configured to apply a mathematical function, such a window, to the data from the combining of the first acceleration and quaternion, to remove noise/errors that contribute to drift, more preferably the apparatus is configured to estimate a direct current component of noise/errors in the result(s) from the combining of the first acceleration and quaternion and configured to select the mathematical function based on the estimate in order to remove it and/or the mathematical function is a Hanning window and/or wherein the apparatus is configured to apply the mathematical function after applying the filter.

Preferably the processor is programmed to provide an acceleration in the vertical direction, such as from the product of the quaternion and the first acceleration. preferably with the vertical direction being the direction of the acceleration of gravity.

Preferably the processor is programmed to subtract the acceleration of gravity from the calculated acceleration to measure the acceleration of the inertial sensing device in the vertical direction of the global reference frame, such as where the calculation the acceleration of gravity is taken from readings by the inertial sensing device which apparatus has recorded in a memory when it is stationary and/or wherein apparatus is configured to measure speed of the inertial sensing device in the vertical direction of the global frame by integrating the calculated acceleration, preferably wherein the acceleration is filtered and/or de-drifted before integration and/or wherein the processor is programmed to integrate the obtained acceleration in the vertical direction twice to measure changes in the vertical position in a global reference frame, preferably on the earth's surface with the vertical direction being the direction of the acceleration of gravity.

Preferably wherein the obtained data is filtered and/or de-drifted before both integrations.

Preferably wherein the processor is programmed to integrate data using Simpson's rule, preferably on all of the acceleration and/or speed data at once.

Preferably wherein the first acceleration is in the form of a vector such as in three dimensions, more preferably the quaternion is in the form of a four by three matrix and is multiplied by the first acceleration vector to provide an acceleration vector in the global reference frame from which the measure of vertical displacement, or a derivative of vertical displacement is calculated. Preferably still wherein the quaternion matrix is of the form $$R_{(q)} = \begin{bmatrix} (q_0^2+q_1^2-q_2^2-q_3^2) & (2q_1q_2-2q_0q_3) & (2q_1q_3+2q_0q_2) & 0 \\ (2q_1q_2+2q_0q_3) & (q_0^2-q_1^2+q_2^2-q_3^2) & (2q_2q_3-2q_0q_1) & 0 \\ (2q_1q_3-2q_0q_2) & (2q_2q_3+2q_0q_1) & (q_0^2-q_1^2-q_2^2+q_3^2) & 0 \\ 0 & 0 & 0 & (q_0^2+q_1^2+q_2^2+q_3^2) \end{bmatrix}$$

with $q_0$ as real value and $q_1$, $q_2$ and $q_3$ as complex numbers

Preferably the processor is programmed to calculate a quaternion when the inertial sensor is at a rest, at least in the vertical direction, from the output acceleration from the inertial sensing device together with the expected acceleration of gravity in the vertical direction of the global reference frame, to store this quaternion in the memory and to use it in deriving the quaternion corresponding to the rotation of the inertial sensing device.

Preferably wherein one of the dimensions of the acceleration vector on the global frame represents a direction parallel to the direction of gravity the value of which is taken as the vertical acceleration.

Optionally wherein the processor comprises multiple microprocessors in communication with each other.

There can be provided vertical jerk measuring apparatus comprising apparatus according to an aspect of the invention wherein the processor is programmed to differentiate the obtained acceleration with respect to time in the vertical direction to measure the jerk in the vertical direction in a global reference frame, preferably on the earth's surface with the vertical direction being the direction of the acceleration of gravity.

There can be provided estimated vertical Centre of Mass movement measuring apparatus comprising apparatus according to an aspect of the invention and comprising a fastening for fastening the inertial sensing device to the back of an animal, preferably a person, and wherein in use when the device is fastened to an estimated measure of the centre of mass of a moving object such as a person the apparatus measures vertical displacement, or a derivative of vertical displacement, of the centre of mass in a global reference frame, preferably wherein the fastening comprises adhesive tape and/or which in use, when the device is fastened to the centre of mass of a moving object, such as a person, measures acceleration and vertical displacement, of the centre of mass in a global reference frame and the processor is programmed to use this data along with the input mass of the object, and preferably also the direction of gravity, in calculating a measure of at least some of the energy used during the movement.

There can be provided human gait monitoring apparatus comprising apparatus according to an aspect of the invention apparatus which in use calculates one or more and preferably all of the jerk, acceleration, speed, change in position of the centre of mass of a person and estimated mechanical energy expenditure, the inertial sensing device being configured to be attachable to a person in a location substantially close to their centre of mass such as adjacent the fourth lumbar vertebra.

According to an aspect of the invention there is provided a method of measuring vertical displacement, or a derivative of vertical displacement, in a global reference frame, comprising the steps of: applying an inertial sensing device at a desired location or to an object the movement of which it is desired to measure; calculating a quaternion corresponding to the rotation of the inertial sensing device and a first acceleration from the outputs of the inertial sensing device, and combining, preferably via a product, the quaternion and acceleration.

Preferably the method comprising one or more features or steps corresponding to the preferable features of the other aspects of the invention.

BRIEF DESCRIPTION OF THE SEVERAL VIEWS OF THE DRAWINGS

Embodiments of the invention will now be described, by way of example only, with reference to the following figures.

DETAILED DESCRIPTION OF THE INVENTION

Figure 1:
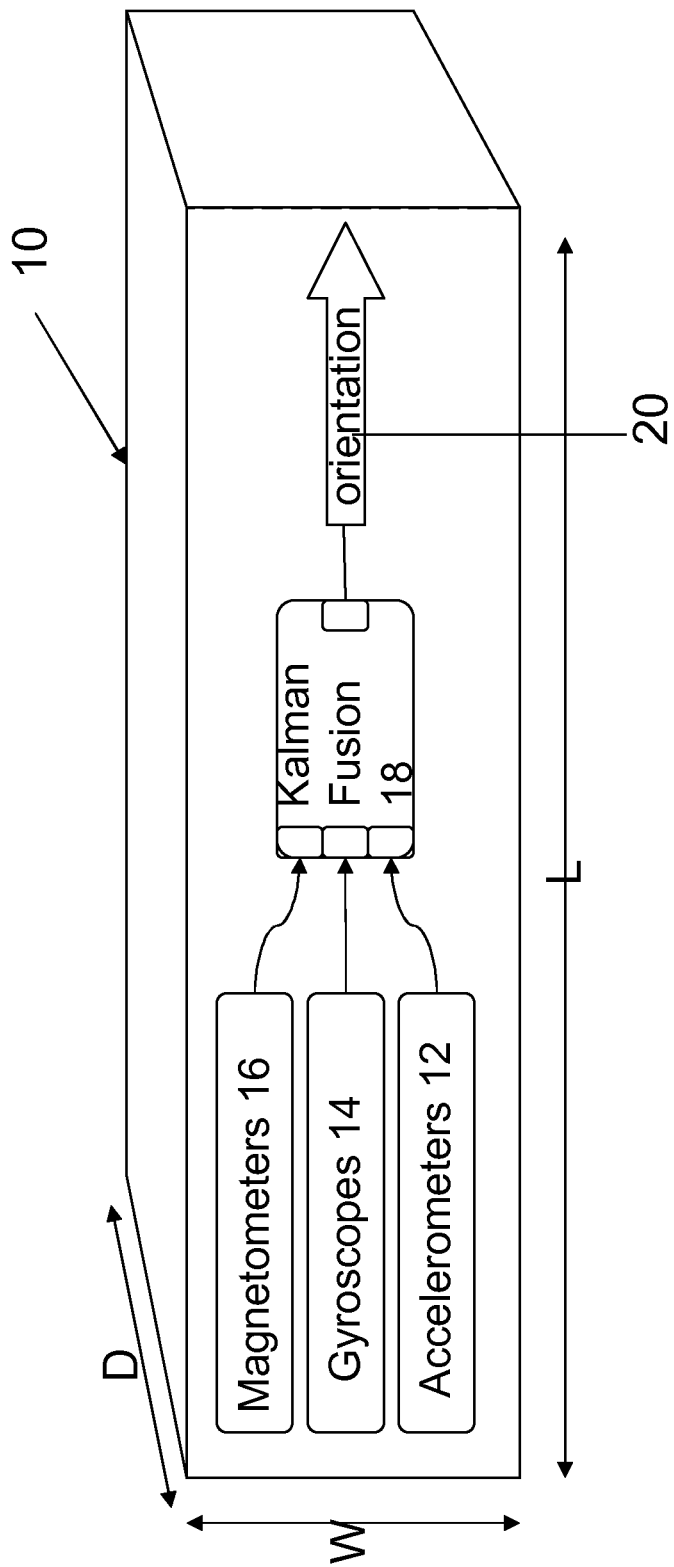
FIG. 1 is a schematic illustration of an inertial measurement unit.

Referring to FIG. 1, there is shown an MEMS inertial measurement unit (IMU) 10 of a type known in the prior art. The IMU 10 comprises accelerometers 12 gyroscopes 14, and magnetometers 16, together with a Kalman fusion processor/integrated circuit 18 and an output 20.

The accelerometers 12 comprise three accelerometers positioned so that the measurement axis of each are orthogonal to the axes of the other two. Each accelerometer measures inertial acceleration in the direction of their own axis. The gyroscopes 14 are also placed in an orthogonal pattern along three measurement axes which may be parallel to the three axes of the accelerometers 12, or at least orientated relative to them at a known angle. The gyroscopes measure rotational position in relation to a local object co-ordinate system. The magnetometers 16 are optional and are not always contained in IMUs. For the purpose of this invention IMU 10 can be used without magnetometers 18. The magnetometers 18 measures the strength of magnetic field, the use of which will vary on its application. For instance the magnetometer can be used to work out the position of the IMU in relation to the Earth's magnetic field, whereas in the case of space exploration it will be used to measure local magnet fields. Magnetometers may also take advantage of magnetic fields that are usually observed indoors.

The processor or integrated circuit 18 is programmed or hard coded with mathematics to take outputs from all of the accelerometers 12, gyroscope 14 and magnetometer 16 and to produce orientation information from them and send this information to the output 20. Typically this program for fusing together the two or three inputs is based on Kalman fusion. This output information then informs users of the orientation of the IMU 10. For example, this can be displayed on a computer screen with a graphical construction of a box of roughly the same shape as the IMU and can be displayed in real time rotating on screen in the same manner and by the same angle as the IMU 10 is rotating.

This orientation information can be used for various application such as measuring vibrations or in space exploration. Recently they have been used to measure angles and movement in bio-mechanics, such as the way in which a knee or elbow bends.

The illustrated IMU is a very typical shape of conventional IMUs. As can be seen it is a cuboid (or might often be another parallelepiped) with its length in one direction 'L' being considerably longer than its width in a second direction 'W' and its depth in a third direction 'D'. Typically the IMU 10 is used flat against a surface that is parallel to the earth surface with depth axis 'D' being substantially parallel with vertical direction in the global reference frame, i.e., in the direction of gravity on earth.

Figure 2:
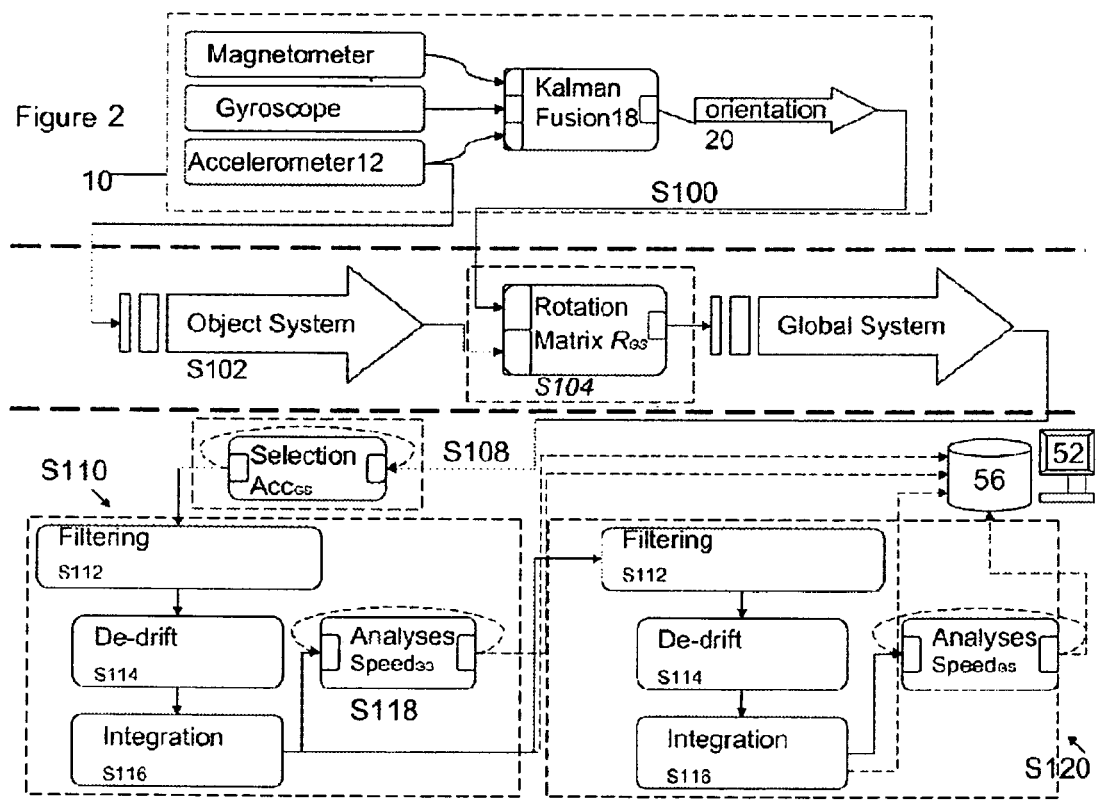
FIG. 2 is a schematic depiction of an apparatus in accordance with the invention in use on a person.

In FIG. 2 there is shown an apparatus 50, which is an embodiment in accordance with the invention. The apparatus 50 comprises a computer 52, including a processor 54 and memory 56, connected via a communication channel 58 to an IMU 10. The computer may be an ordinary general purpose computer or multiple computers connected together. The memory 56 may include random access memory and preferably includes some permanent storage device such as a hard disk or both The IMU 10 is fastened into the lumbar region of the back of a person P and is located as close as practicable to the estimate of the human centre of mass. The fastening mechanism may simply be tape 11. The IMU 10 may be taped adjacent the fourth lumbar vertebrate.

In use the person P then walks backwards and forwards.

As can be seen the IMU 10 is not flat against a surface with the direction of axis 'D' in line with the direction of gravity but instead the IMU 10 is twisted by close to 90 degrees so that the axis closest to being in line with the direction of gravity is the length axis 'L'. Even the L axis is not parallel with gravity because of the curvature of the back. As the person walks the IMU 10 all three axes move relative to the global reference frame, often in complex movements.

Modern IMUs often rely on MEMS (micro-electro mechanical systems). In this instance an IMU that can be used includes the Xsens manufactured at Enschede in the Netherlands.

Also shown in FIG. 2 are the local axes of the IMU W, D and L and the axes X, Y, Z, of the global reference system which in this case corresponds to the normal frame of objects on the Earth, with the X and Y axes being along the plane of the surface of the earth and the Z axis being in the direction of gravity. With the position of the person P these axes are in line with the standard axes for human gait which are defined as, x being forward movement in the transverse plane perpendicular to the frontal plane, y pointing to the left in the transverse plane perpendicular on the sagittal plane and z upwards vertical movement in the frontal plane perpendicular to the transverse plane. The IMU 10 is taped as centrally with respect to the width of the back as possible, to maximise sensitivity to asymmetry in movements in the frontal plane.

The information which is received from the Kalman fusion processor 18 of the IMU 10 relates to orientation based on the local axes W, D and L. Similarly data taken from the accelerometers 12 relates to accelerations along the three local axes W, D and L. These accelerations already contain some error and if the wrong procedure is used to convert these accelerations into accelerations in the global X, Y, Z frame then these errors will increase further. Error in accelerations will increase further still if they are integrated inappropriately to find the speed and changing position.

Figure 3:
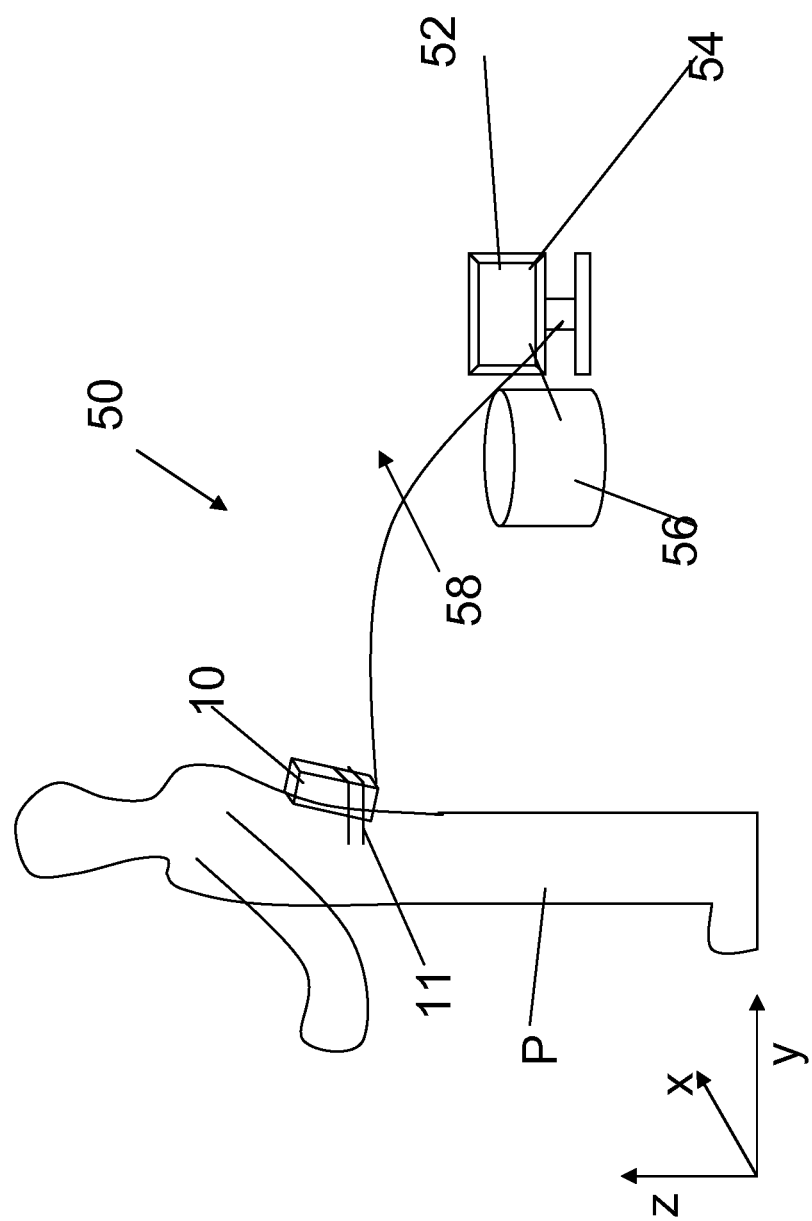
FIG. 3 is a flow chart of method in accordance with the invention using apparatus in accordance with the invention.

In FIG. 3 there is shown the IMU 10 together with the computer 52 and memory 56 together with processes used in accordance with the invention. At step S100, orientation information is taken from the output 20 of Kalman fusion processor 18 and at step S102 accelerations in the object reference frame W, D, L are taken directly from the accelerometers 12.

Next at step S104 the orientation data from step S100 from the fusion processor 18 is used to form a rotation element.

Previous attempts to use IMUs in biomechanics have used Euler angle based rotation matrices. It has been found that this choice is one cause of the lack of accuracy in output data and in the case of attempting to measure data from an IMU 10 taped at close to 90 degrees to the fourth lumbar vertebra of a person, a Euler angle rotation matrix can lead to grossly inaccurate data.

It has been realised that the type of rotations applied to the IMU 10 during a normal persons walking gait coupled with the orientation of the IMU to start with leads to significant incidences of mathematical gimbal lock if Euler angle rotational measurements are used. This leads to lost information. It has been found that much more accurate information can be obtained using a quaternion based rotational element instead. Quaternions have previously been used in space engineering and virtual reality but has not previously been considered of significance to biomechanics or used in rotating accelerations from the object frame of an IMU into vertical accelerations in the global reference frame.

The computer 50 includes software program instructions in accordance with the invention in its memory 56. The programmed computer 50 can for instance run LabVIEW 8.5.1 to transpose the accelerations from the object system, in step S102 onto the orthogonal global reference system X, Y, Z, using a quarternion matrix calculated from the data from output 20. An example of such an equation shown below:

$$a_{(gs)}\begin{bmatrix} x \\ y \\ z \end{bmatrix} = a_{(os)}\begin{bmatrix} x \\ y \\ z \end{bmatrix} \cdot R_{(q)} \begin{bmatrix} q_0 \\ q_1 \\ q_2 \\ q_3 \end{bmatrix}$$

Where $a_{(gs)}$ is the linear acceleration in the global system, $a_{(os)}$ is the linear acceleration in the object/local system displayed as a 3×1 matrix and $R_{(q)}$ is the quaternion rotation matrix with $q_0$ as real value and $q_1$, $q_2$ and $q_3$ as complex numbers combined in a 4×3 matrix. A suitable rotation matrix $R_{(q)}$ is shown below:

$$R_{(q)} = \begin{bmatrix} (q_0^2 + q_1^2 - q_2^2 - q_3^2) & (2q_1q_2 - 2q_0q_3) & (2q_1q_3 + 2q_0q_2) & 0 \\ (2q_1q_2 + 2q_0q_3) & (q_0^2 - q_1^2 + q_2^2 - q_3^2) & (2q_2q_3 - 2q_0q_1) & 0 \\ (2q_1q_3 - 2q_0q_2) & (2q_2q_3 + 2q_0q_1) & (q_0^2 - q_1^2 - q_2^2 + q_3^2) & 0 \\ 0 & 0 & 0 & (q_0^2 + q_1^2 + q_2^2 + q_3^2) \end{bmatrix}$$

Before motion of the person P is measured the subject person P is preferably asked to stand rigid for a time, e.g., 3 seconds, in order to take base-line gravitational measurements. Since the output 20 generates a value for $a_{(os)}$ and it is known that the z component of $a_{(gs)}$ during rest should be equal to −1 G or −9.81+/−0.2 ms$^{-2}$ it is possible to calculate suitable values for $R_{(q)}$ using the equation above. These values can then be used as a basis for step 104 when the quaternion matrix is calculated from the orientation data during motion.

The equation above is then used to transpose the $a_{(os)}$ to the global frame during motion of the person P From step S104 is obtained accelerations in the global reference frame of which the acceleration of most interest being the acceleration in the Z axis. because of the steps taken before motion it is known that the Z axis is in the direction of gravity. At step S106 an average of gravitational force during rest (i.e., −1 G approximately −9.81+/−0.2 ms$^{-2}$) is subtracted from the calculated Z axis linear acceleration. Rather than simply rely on a known value for 'G' the data taken when the subject person P stands erect can be used for accurate subtraction.

Step S106 provides information relating to the acceleration in the vertical direction. At step S110 a number of processes are applied to improve the accuracy of the acceleration measurement and to obtain the speed measurement in the Z direction.

First at step S112 a filter is applied to the acceleration data. It has been found that a fourth order Butterworth low pass filter is particularly effective. Crucially the sensors in the IMU 10 cannot distinguish between vibrations and real movements relating to the gait of the subject. To remove such unwanted vibrations accelerations above a certain frequency are filtered out. Typically the Butterworth filter is used to filter out accelerations above 25 Hz. Components of walking/gait do not occur at faster frequencies than 25 Hz and therefore any information or frequency above this would not appear to relate to walking patterns.

After filtering the data is de-drifted at step S114. IMUs such as IMU 10 suffer from drift in the output data thought to be due to natural biases in the sensors. Over time this drift can significantly skew results. Since its wished to measure walking gait over some time period it is important therefore that the data is de-drifted so that this drift which occurs increasingly over time does not damage the results.

From the data output it is possible to look at the shape of the drift and from this estimate the direct current component. For instance frequency analysis can be performed on a plot of the data to calculate the drift. Once this DC estimate is obtained it can be subtracted from the data by applying a window and hence remove much of the drift. It has been found that a Hanning window e.g. of 3 points, such as described for use by Katićet at in 'Application-Oriented Comparison of the Methods for AC/DC Converter Harmonics Analysis' (published in IEEE Transactions of Industrial Electronics Vol. 50 No. 6, December 2003), is particularly effective.

After filtering and de-drifting steps S112 and S114 it has been found that it is then possible to integrate the acceleration data to find speed data without increasing the error too significantly as is commonly the case with use of data from accelerometers. In particular problems caused by drift increase after integration.

At step S116 the data is integrated. There are a huge different number of ways of integrating data and in traditional approaches using IMUs it has been common to break the data up into small steps in an attempted to integrate these separately. With the present invention it has been found that use of Simpson's rule provides good results even when applied at once to the whole data set. The suitability of the integration method was able to be verified by consultation with experts on bio-mechanical movement who have knowledge of expected results and access to databases of bio-mechanical movement and therefore know what the resultant speed from the integration should look like. From this step S116 is then provided the speed in the global system in the Z direction at step S118.

In order to provide the relative change position in the global Z access at step S120, the steps S112, S114 and S116 are all repeated. Importantly by filtering de-drifting and integrating using Simpson's rule the errors are not increased too significantly when moving from speed to a relative change of position. Commonly when attempting to analyse the data from accelerometers, the error present by the time that position is calculated is often too great to be useful.

The acceleration, speed and position are all measured over a time period t and their calculated values from steps S106, S118 and S120 are all independently stored in the memory 56.

A further step S122 can be added, repeating steps S112-S118 to find the derivative of the acceleration with respect to time. This value is often called "jerk" and is of use in clinical care and elsewhere.

For calculation of the energy used by person P in walking or running the acceleration data from step S106 is used along with the position vector calculated from data from steps S120. Since the mass of the person remains constant whilst walking the work done in the z direction can be calculated from the person's mass and the integral of the acceleration with respect to the position in the z direction together with work done against gravity calculated from the position in the z directions (change in height from the ground). From these calculations it can be found how much energy has been used in moving the centre of mass vertically. Whilst this accounts for most of the energy expended it does not account for all of it and therefore further adaptations are made to estimate total energy. This may be for example, to add a set amount of J/kg to the initial calculation or to increase the calculated value by a set percentage. The total energy acting on the estimated centre of mass can also be calculated from the speed and displacement information, deriving kinetic energy using $\frac{1}{2} mv^2$ and potential energy using mgh Knowing these parameters the external work performed and efficiency of energy transformations during walking can be calculated. Alternatively only some of the data above is used for the estimate such as by only using the estimate of work done against gravity.

Alternatively the energy can be estimated by coupling measured vertical data with empirical information. The conventional method of using a pedometer uses the measure of how many strides have been taken together with looking up from empirical data how much energy an average person of that weight uses per stride. Similarly it would be possible to build up empirical data of gait patterns measured using apparatus 50 against energy measured by some other means (such a heart rate monitor). Applying apparatus 50 with this stored data provides a more accurate estimate of energy than stride number and weight alone can provide.

Data gathered from an example of an embodiment in accordance with the invention are shown below. To produce this data, 4 men and 1 woman aged 23.4+/−3.8 years and weighing 80.5/−14.3 kg and having a height of 181+/−5.4 cm were used. As well as measurements and calculations from the IMU in accordance with the invention, a reflective marker was placed on the middle of the IMU to measure displacement with an OMCS which in this instance was the Qualisis Proreflex system from Stockholm, Sweden. Both the apparatus 50 and the known OMCS were synchronised and measured a sample frequency of 100 Hz. Each person measured was allowed to walk at their self selected walking speed SSWS.

Position data of the OMCS was smoothed by using a Savitzky-Golay smoothing filter[14] with a window of 5 points. Acceleration was symmetrically derived from position by using $\vec{a}_z=(\Delta^2 \vec{r}_z/\Delta t^2)$. Where $\vec{a}$ represents the linear acceleration in the orthogonal frame, and $\vec{r}$ represents the position of the reflective marker in the calibrated orthogonal frame.

Peak amplitudes of the z-axis were extracted from the data sets from both the embodiment of the invention 50 and the OMCS and imported into SPSS 14 for Windows. The data sets were compared using a paired sample t-test and a Two-Way Mixed effect with consistency Intra Class Correlation Test (ICC) according to McGraw et al (Forming Inferences About Some Intraclass Correlation Coefficients. *Psychological Methods* 1996; 1(1):30-46), defined as the mean of differences between tests and standard deviation were calculated. Also a partial linear correlation test between the speed in the x-axes and the BIAS was performed. Adequate test-retest reliability has been defined as ICCs≥0.75 for continuous variables.

Relative peak and trough difference of velocity and position of the CoM in the vertical axes were calculated for both systems and compared using a paired sample t-test. A Two-Way ICC was performed as previously described. Error described as the relative difference in speed and position of the OMCS subtracted from the IMU error was calculated for as many peaks and troughs visible in both data sets.

Data from these steps collected from IMU and OMCS over three walks for each subject including the standard deviation calculated over the three walks, are displayed in FIGS. 4a, 4b, 4c and in the following table

| Subject | $\Delta a_{IMU}$ (ms−2) | $\Delta a_{OMCS}$ (ms−2) | $\Delta v_{IMU}$ (ms$^{-1}$) | $\Delta v_{OMCS}$ (ms$^{-1}$) | $\Delta p_{IMU}$ (cm) | $\Delta p_{OMCS}$ (cm) |
|---|---|---|---|---|---|---|
| 1 | 2.16 ± 0.30 | 2.36 ± 0.26 | 0.40 ± 0.06 | 0.44 ± 0.06 | 4.11 ± 0.40 | 4.22 ± 0.44 |
| 2 | 2.65 ± 0.26 | 2.70 ± 0.20 | 0.57 ± 0.05 | 0.57 ± 0.04 | 5.08 ± 0.29 | 4.99 ± 0.40 |
| 3 | 1.75 ± 0.17 | 1.92 ± 0.18 | 0.36 ± 0.01 | 0.36 ± 0.01 | 3.34 ± 0.27 | 3.34 ± 0.07 |
| 4 | 1.58 ± 0.09 | 1.83 ± 0.10 | 0.31 ± 0.05 | 0.35 ± 0.04 | 3.24 ± 0.38 | 3.33 ± 0.36 |
| 5 | 2.38 ± 0.08 | 2.64 ± 0.09 | 0.45 ± 0.01 | 0.47 ± 0.05 | 4.42 ± 0.13 | 4.43 ± 0.48 |

The table shows the average error over 3 walks for 5 healthy subjects of acceleration, velocity and relative position change in the z-axis. Error is calculated as being the relative difference in speed and velocity of the IMU subtracted by the relative difference in speed and velocity in the OMCS. The error is shown in FIG. 4 on the right hand axis.

Figure 4A:
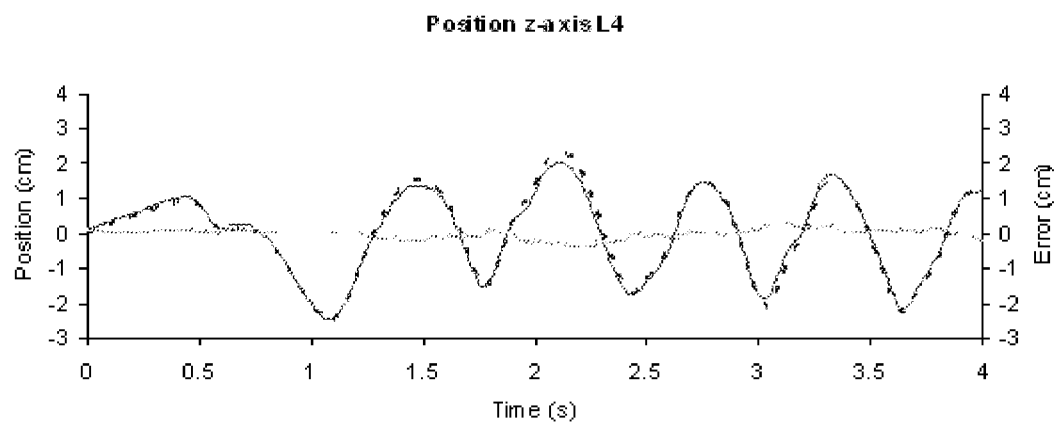
FIGS. 4a, 4b and 4c are graphs of the data from a comparison of an embodiment in accordance with the invention and a conventional OMCS system.

In FIG. 4a is shown the acceleration data from the apparatus 50 and from the OMCS. As can be seen from this figure and from the table the data between the IMU and OMCS acceleration shows good agreement between the OMCS and IMU. Z-axis amplitudes from the IMU (2.1±1.2 ms$^{-2}$) and the optical motion capture system (2.3±1.2 ms$^{-2}$) were not significantly different (p≥0.05) indicating agreement between systems. In addition ICC=0.952 and random error 0.176 ms$^{-2}$ also demonstrates strong agreement between systems. The partial linear correlation among subjects, between speed in the x-axis in the orthogonal system and the BIAS were not correlated (r=0.065).

Figure 4B:
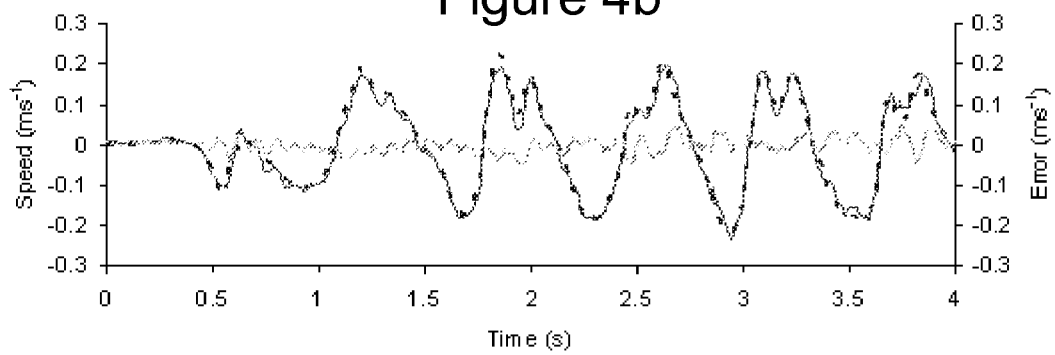
Figure 4C:
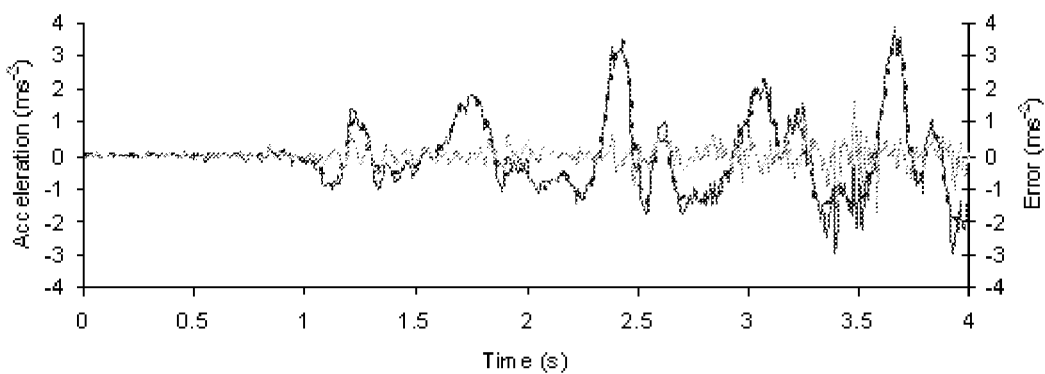

FIG. 4b shows the speed from the two pieces of apparatus A paired sample t-test between the relative change in speed (peak to peak) in the OMCS and IMU shows a significance difference (p<0.05). A Two-Way Mixed ICC was performed as previously described and showed a highly significance between the IMU and OMCS (ICC=0.888) with a random error of 0.121 ms$^{-1}$. Error described as the relative difference in speed OMCS subtracted from the IMU is shown in the following table as the mean value over 3 walks between subjects.

| Error in z-axis IMU-OMCS over three walks | | | | |
|---|---|---|---|---|
| Subject | a (ms$^{-2}$) | v (ms$^{-1}$) | p (cm) | Steptime (s) |
| 1 | −0.197 | −0.037 | −0.026 | −0.064 |
| 2 | −0.050 | −0.004 | −0.128 | 0.108 |
| 3 | −0.260 | 0.006 | 0.002 | 0.100 |
| 4 | −0.268 | −0.039 | −0.091 | 0.015 |
| 5 | −0.174 | 0.014 | 0.008 | 0.377 |
| avg | −0.190 | −0.012 | −0.047 | 0.107 |
| std | 0.088 | 0.025 | 0.060 | 0.166 |

Measurement of change in position is shown in FIG. 4b. A paired sample t-test between the relative change in position (peak to peak) in the OMCS and IMU shows no significant difference (p≥9.05). A Two-Way Mixed ICC shows a highly significant correlation (ICC=0.782) with a random error of 1.35 cm.

Steptime calculated as the difference in time between troughs of position measured by the IMU and OMCS is shown in the table below

| Subject | Steptime$_{IMU}$ (s) | Steptime$_{OMCS}$ (s) |
|---|---|---|
| 1 | 0.598 ± 0.01 | 0.591 ± 0.02 |
| 2 | 0.572 ± 0.01 | 0.571 ± 0.01 |
| 3 | 0.632 ± 0.01 | 0.633 ± 0.01 |
| 4 | 0.615 ± 0.01 | 0.616 ± 0.01 |
| 5 | 0.579 ± 0.02 | 0.567 ± 0.03 |

This showed no significant difference (p≥9.05). A Two-Way Mixed ICC showed a highly significant correlation (ICC=0.757) with a random error of 8.62 ms.

Whilst the results show no significant difference of acceleration but some significant difference for peak to peak speed and position the differences are in fact far less than might be expected. When it comes to change of position the Z direction in the OMCS ought to be far superior since it measures the position directly whereas the current invention relies on thorough integration from acceleration measurements.

Figure 5:
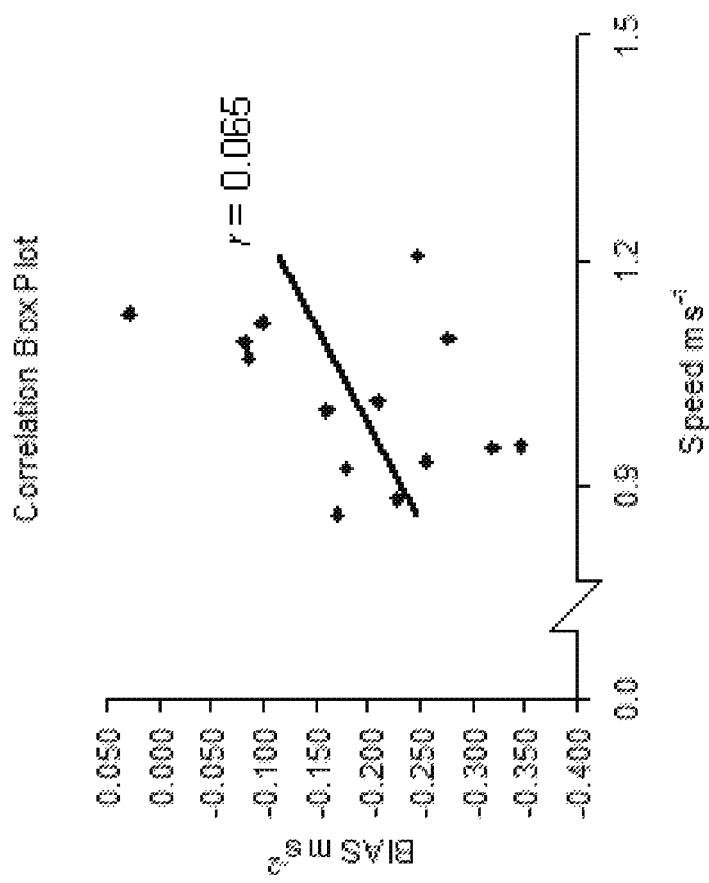
FIG. 5 shows a Correlation Box Plot representing the speed in the orthogonal x axes compared with the BIAS between the peaks of a data from the embodiment in accordance with invention and OMCS compared in FIG. 4.

In FIG. 5 is shown a Correlation Box Plot representing the speed in the orthogonal x axis compared with the BIAS between the peaks of the IMU and OMCS.

For such a small difference in error to be present in the measurement position when compared to the expensive OMCS, appears to demonstrate that the filtering and de-drifting techniques used are extremely effective before integration of the acceleration data and that the translation of the object system accelerations into the global system frame using a quaternion rotation matrix is very effective. Apparatus in accordance with the invention would appear to be therefore an accurate and cheap alternative to OMCS for such acceleration measurements.

In other embodiments of the invention a differently shaped IMU is used which when locating in the curvature of the back can be present at close to zero degrees rather than plus or minus 90 degrees. It is the angle of plus or minus 90 degrees which increases the risk of losing data through mathematical gimbal lock.

The longer the measurement period the less accurate the data will eventually be, but the more significant role that is played by the effective use of de-drifting steps and ensuring that they are used with and preferably before each integration.

The apparatus 50 in accordance with the invention does provide spatiotemporal measurement in human walking that are accurate enough for clinical use. Importantly the method of the invention of assessing human gait by using IMUs is accurate when compared to OMCS for different subjects and that their self selecting walking speed in real world conditions as opposed to merely finding data from subjects walking artificially on a treadmill.

In addition to providing apparatus and method for measuring human CoM kinematics embodiments in accordance with the invention may be used for other uses where vertical position, speed, acceleration jerk, or energy/work information in the global reference frame is useful. For example a computer game controller can include an IMU in a system in accordance with the invention and thereby provide accurate changes in position in the vertical direction for use as an input in a computer game. As well as being useful in the entertainment industry such controllers can be used in simulation programs. The measurements of CoM and energy used can also be applied to other animals and also to inanimate moving objects.

Whilst the embodiments of the invention are generally mentioned above as used to measure vertical movement in the reference frame of the earth's surface embodiments can be used for any global reference frame. As well as the Earth, embodiments of the disclosed invention can be also be used in a very similar way, including the calculations regarding gravity on other bodies with their own significant gravitational field such as the moon, with the z axis corresponding to the bodies gravity and the value of gravitational acceleration being adjusted appropriately.

The invention claimed is:

1. A vertical center of mass movement measuring apparatus comprising: an inertial sensing device having a local frame of reference and arranged to undergo rotation and acceleration in the local frame of reference, for producing outputs relating to said rotation and acceleration in the local frame of reference, and configured for fastening to the back of an animal having a center of mass; a memory; and a processor, wherein the processor is programmed to provide a quaternion corresponding to the rotation of the inertial sensing device and a first acceleration, both based on an output of the inertial sensing device, and the processor is programmed to transform the first acceleration using the quaternion to produce a result, and based on integration of the result to provide an estimate of at least one of a vertical displacement and a derivative of vertical displacement, of the center of mass in a global reference frame.

2. The vertical center of mass movement measuring apparatus according to claim 1 wherein the apparatus is configured to filter the result from the combination of the first acceleration and quaternion.

3. The vertical center of mass movement measuring apparatus according to claim 2 wherein the apparatus is configured to filter data out above a frequency chosen based on maximum stride frequency.

4. The vertical center of mass movement measuring apparatus according to claim 2 comprising a Butterworth filter which filter is configured to be used for the filtering.

5. The vertical center of mass movement measuring apparatus according to claim 1 wherein the apparatus is configured to apply a mathematical function to the result, to remove at least one of noise and errors that contribute to drift.

6. The vertical center of mass movement measuring apparatus according to claim 5 wherein the apparatus is configured to estimate a direct current component of at least one of noise and errors in the result from the combining of the first acceleration and quaternion and configured to select the mathematical function based on the estimate in order to remove it.

7. The vertical center of mass movement measuring apparatus according to claim 5 wherein the mathematical function is a Hanning window.

8. The vertical center of mass movement measuring apparatus according to claim 5 wherein the apparatus is configured to filter the result from the combination of the first acceleration and quaternion and the apparatus is configured to apply the mathematical function after applying the filter.

9. The vertical center of mass movement measuring apparatus according to claim 1 wherein the global reference frame is the reference frame of the earth's surface with the vertical direction being the direction of the acceleration of gravity.

10. The vertical center of mass movement measuring apparatus according to claim 1 wherein the inertial sensing device comprises: at least one of an inertial mass unit and multiple accelerometers measuring linear accelerations in a local frame, and at least one gyroscope measuring rotational movement; and a device which is arranged to fuse their data outputs using Kalman filtering.

11. The vertical center of mass movement measuring apparatus according to claim 1 wherein the processor is programmed to provide an acceleration in the vertical direction, with the vertical direction being the direction of the acceleration of gravity.

12. The vertical center of mass movement measuring apparatus according to claim 11 wherein the processor is programmed to subtract acceleration of gravity from the calculated acceleration to measure the acceleration of the inertial sensing device in the vertical direction of the global reference frame.

13. The vertical center of mass movement measuring apparatus according to claim 11 wherein the apparatus is configured to measure speed of the inertial sensing device in the vertical direction of the global frame by integrating the acceleration in the vertical direction.

14. The vertical center of mass movement measuring apparatus according to claim 13 wherein the apparatus is configured to filter and de-drift the acceleration in the vertical direction before integration.

15. The vertical center of mass movement measuring apparatus according to claim 13 wherein the processor is programmed to integrate data using Simpson's rule.

16. The vertical center of mass movement measuring apparatus according to claim 11 wherein the processor is programmed to integrate the obtained acceleration in the vertical direction twice to measure changes in the vertical position in the global reference frame.

17. A vertical jerk measuring apparatus comprising the apparatus according to claim 11 wherein the processor is programmed to differentiate the obtained acceleration with respect to time in the vertical direction to measure the jerk in the vertical direction in the global reference frame.

18. The vertical center of mass movement measuring apparatus according to claim 1 wherein the first acceleration Is in the form of a vector in three spatial dimensions and the quaternion is in the form of a four by three matrix and is multiplied by the first acceleration vector to provide an acceleration vector in the global reference frame from which at least one of the measure of vertical displacement, and a derivative of vertical displacement, is calculated.

19. The vertical center of mass movement measuring apparatus according to claim 18 wherein the quaternion matrix is of the form $$R_{(q)} = \begin{bmatrix} (q_0^2 + q_1^2 - q_2^2 - q_3^2) & (2q_1q_2 - 2q_0q_3) & (2q_1q_3 + 2q_0q_2) & 0 \\ (2q_1q_2 + 2q_0q_3) & (q_0^2 - q_1^2 + q_2^2 - q_3^2) & (2q_2q_3 - 2q_0q_1) & 0 \\ (2q_1q_3 - 2q_0q_2) & (2q_2q_3 + 2q_0q_1) & (q_0^2 - q_1^2 - q_2^2 + q_3^2) & 0 \\ 0 & 0 & 0 & (q_0^2 + q_1^2 + q_2^2 + q_3^2) \end{bmatrix}$$

with q0 as real value and q1, q2 and q3 as complex numbers.

20. The vertical center of mass movement measuring apparatus according to claim 1 wherein the processor is programmed to calculate a quaternion when the inertial sensor is at a rest, at least in the vertical direction, from the output acceleration from the inertial sensing device together with the expected acceleration of gravity in the vertical direction of the global reference frame, to store this quaternion in the memory and to use it in deriving the quaternion corresponding to the rotation of the inertial sensing device.

21. The vertical center of mass movement measuring apparatus according to claim 1, wherein the processor is programmed to use at least one of the estimate of vertical displacement and a derivative of vertical displacement of the center of mass, along with the input mass of the moving object, and also the direction of gravity, in calculating a measure of at least some of the energy used during the movement.

22. A computer program product containing instructions which when run on a processor connected to a memory and inertial sensing device provides the apparatus according to claim 1.

23. A vertical center of mass movement measuring apparatus comprising: an inertial sensing device, for producing outputs relating to rotation and acceleration in its local frame of reference, a memory and a processor, wherein the processor is programmed to provide a rotation element corresponding to the rotation of the inertial sensing device and a first acceleration, both based on an output of the rotation sensing device, and the processor is programmed to transform the first acceleration using the rotation element and based on integration of the result of the transformation to provide a measure of vertical displacement, or a derivative of vertical displacement, in a global reference frame, wherein the apparatus is configured to apply a mathematical function to the data from the combining of the first acceleration and rotation element to remove noise/errors that contribute to drift.

* * * * *